United States Patent [19]

Wang et al.

[11] Patent Number: 5,359,023
[45] Date of Patent: Oct. 25, 1994

[54] CYCLOHEXANENORBORNANE EPOXY RESIN WITH CURING AGENT

[75] Inventors: Pen-Chung Wang, Houston; Donald R. Kelsey, Fulshear, both of Tex.

[73] Assignee: Shell Oil Company, Houston, Tex.

[21] Appl. No.: 184,539

[22] Filed: Jan. 21, 1994

Related U.S. Application Data

[62] Division of Ser. No. 29,192, Mar. 10, 1993, Pat. No. 5,284,929.

[51] Int. Cl.$^5$ .............. C08G 59/04; C08G 59/50; C08G 59/62
[52] U.S. Cl. .............................. 528/97; 525/481; 525/523
[58] Field of Search ................................. 528/97

[56] References Cited

U.S. PATENT DOCUMENTS

| | | | |
|---|---|---|---|
| 3,410,825 | 11/1968 | Coover, Jr. et al. | 528/97 |
| 3,536,734 | 10/1970 | Vegter et al. | 260/348.6 |
| 4,663,400 | 5/1987 | Wang et al. | 528/97 |
| 4,764,571 | 8/1988 | Namba et al. | 525/534 |
| 4,855,385 | 8/1989 | Cavitt | 528/97 |
| 5,095,082 | 3/1992 | Kelsey | 526/282 |
| 5,151,471 | 9/1992 | Qureshi et al. | 528/97 |

FOREIGN PATENT DOCUMENTS

| | | | |
|---|---|---|---|
| 1-135858 | of 0000 | Japan | 528/97 |
| 61-168618 | 7/1986 | Japan | 528/97 |
| 62-39616 | 2/1987 | Japan | 528/97 |

*Primary Examiner*—Robert E. Sellers

[57] ABSTRACT

An epoxy resin is provided which can be described by the formula

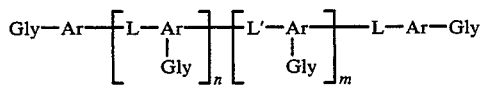

in which Ar is an aromatic moiety, L is a divalent cyclohexanen or bornane linking moiety, L' is a divalent cycloaliphatic moiety, Gly is a glycidyl ether group, and each of m and n is a number within the range of 0 to about 10. Such epoxy resins include the product of glycidation of the product of the addition reaction of a phenol and a cyclohexenenorbornene compound such as 5-(3-cyclohexen-1-yl)bicyclo[2.2.1]hept-2-ene. The resulting epoxy resins have low melt viscosity and low water absorbance in the cured state and are useful as the resinous component of high-performance electrical laminating and encapsulation formulations.

4 Claims, No Drawings

CYCLOHEXANENORBORNANE EPOXY RESIN WITH CURING AGENT

This is a division, of application Ser. No. 029,192, filed Mar. 10, 1993, now U.S. Pat. No. 5,284,929.

BACKGROUND OF THE INVENTION

This invention relates to novel thermosettable epoxy resins.

Epoxy resins are a class of thermosettable materials having wide application in structural, coating and electronic applications. For high-performance electronic applications, such as circuit boards for high-speed computers, epoxy resins having increasingly low melt viscosity (for ease and speed of processing during the pre-pregging stage of electrical lamination preparation) and low water absorbance in the cured state are required.

It is therefore an object of the invention to provide an epoxy resin having low melt viscosity and low water absorption in the cured state.

SUMMARY OF THE INVENTION

According to the invention, an epoxy resin is provided which can be described by the formula

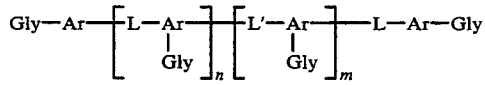

in which Ar is an aromatic moiety, L is a hexanenorbornene linking moiety, L' is a divalent cycloaliphatic moiety, Gly is a glycidyl ether group, and each of m and n is a number within the range of 0 to about 10. Such epoxy resins include the product of glycidation of the product of the addition reaction of a phenol and a cyclohexenenorbornene compound such as 5-(3-cyclohexen-1-yl)bicyclo[2.2.1]hept-2-ene. The resulting epoxy resins are useful as the resinous component of electrical laminating and encapsulation formulations.

DETAILED DESCRIPTION OF THE INVENTION

The invention epoxy resins can be prepared by reacting the precursor polyphenols (described below) with an epihalohydrin such as epichlorohydrin in the presence of a catalyst such as a quaternary ammonium salt or phosphonium halide, followed by dehydrochlorination under reduced pressure in the presence of aqueous caustic. The reaction can be carried out at a temperature within the range of about 40° to about 120° C., preferably about 80° to about 110° C.

The precursor polyphenols can be described by the formula

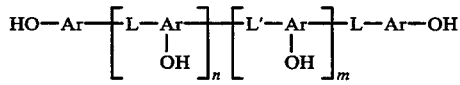

in which Ar is a $C_{6-20}$ aromatic moiety, L is a divalent cyclohexanenorbornane linking moiety, L' is a divalent cycloaliphatic moiety, and each of m and n is a number within the range of 0 to about 10. Such polyphenols can be prepared by the addition reaction of a phenol with a cyclohexenenorbornene compound such as 5-(3-cyclohexen-1-yl)bicyclo[2.2.1]hept-2-ene (herein referred to as the "cyclohexenenorbornene" compound).

Suitable phenols include mono- and polynuclear phenols having at least one unsubstituted position ortho- or para- to a phenolic hydroxyl group, such as phenol, cresol, 3,4- and 3,5-dimethylphenol, resorcinol, biphenol, 1-naphthol and hisphenol A or F. Phenol is preferred.

Suitable cyclohexenenorbornene compounds include

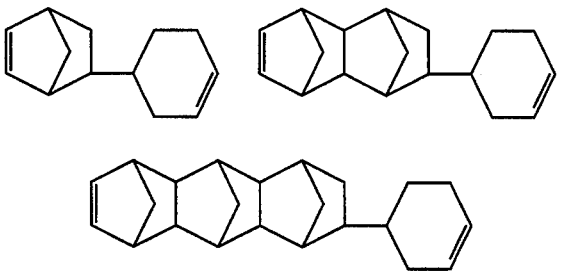

referred to herein as "monoadduct," "diadduct" and "triadduct," respectively, and isomers thereof.

The starting phenol can also include a derivative L' of a cycloaliphatic diene such as dicyclopentadiene, cyclopentadiene, norbornadiene dimer, norbornadiene, methylcyclopentadiene dimer, limonene, 1,3- and 1,5-cyclooctadiene, α- and γ-terpinene, 5-vinylnorbornene, 5-(3-propenyl)-2-norbornene and cyclopentadiene oligomers, for example.

The cyclohexenenorbornene compound is an addition product of 4-vinylcyclohexene and cyclopentadiene which can be prepared by contacting 4-vinylcyclohexene and dicyclopentadiene, preferably in the presence of a polymerization inhibitor such as t-butyl catechol, at a temperature of at least about 150° C., preferably about 180° to 260° C., for a time within the range of about 2 hours to about 8 hours. Under these conditions, the dicyclopentadiene is cracked to cyclopentadiene, and the vinylcyclohexene and cyclopentadiene undergo an addition reaction to produce a mixture of mono-, di- and poly-adducts as well as cyclopentadiene oligomers (e.g., trimer, tetramet, pentamer, etc.). For recovery of one or more desired compounds, the reaction product mixture containing predominately 5-(3-cyclohexen-1-yl)bicyclo[2.2.1]hept-2-ene is allowed to cool to about 50°–70° C. and is stirred under reduced pressure to strip off unreacted vinylcyclohexene. The reaction product is then purified by fractional vacuum distillation for removal of unwanted by-products including, optionally, di- and polyadducts, and the purified product is passed through an adsorbent bed for removal of t-butyl catechol. Preparation of a vinylcyclohexene/cyclopentadiene adduct is illustrated in Example 1 herein.

The phenolic precursors of the invention epoxy resins can be prepared by contacting, under addition reaction conditions, the above-described vinylcyclohexene/cyclopentadiene adduct with a molar excess, preferably about 10 to about 30 moles, of the selected phenol per mole of the adduct. The reaction is most efficiently carried out in the presence of a Lewis acid such as $BF_3$, coordination complexes thereof such as boron trifluoride etherate, $AlCl_3$, $FeCl_3$, $SnCl_4$, $ZnCl_2$, silica and silica-alumina complexes and at an elevated temperature within the range of about 70° to about 200° C., preferably about 100° to about 180° C. The reaction is continued until the desired degree of reaction has been completed, usually for a time within the range of about 30 minutes to about 10 hours, preferably about 1 hour to about 3 hours. Preparation of such polyphenols is illustrated in Examples 2 and 4 herein. Glycidation of the resulting polyphenols to prepare the invention epoxy resins is described above and in Examples 3 and 5 herein.

The invention epoxy resins can be combined with a curing agent and cured by exposure to elevated temperature within the range of about 150° to about 250° C. for a time which can vary widely depending on the cure schedule and thickness of the part, generally greater than about 0.25 hour. Suitable curing agents include amines such as diaminodiphenyl sulfone and methylene dianiline, and phenols such as phenolic novolacs and the precursor phenols for the invention epoxy resins. Optimum properties in the cured resin can be achieved by a staged heating process employing higher temperature in each stage, as illustrated in the Examples 3 and 5 below. The epoxy resins can be co-cured with other thermosettable resins such as bismaleimides and cyanate esters, for example.

The invention epoxy resins are useful, for example, in electrical laminates, structural composites and molding compounds.

EXAMPLE 1

Preparation of 5-(3-cyclohexen-1-yl)bicyclo[2.2.1]hept-2-ene

Dicyclopentadiene and 4-vinylcyclohexene in equimolar mixture were heated in an autoclave at 240° C. for 4–4.5 hours. The reaction product was diluted with cyclohexane and passed through a packed bed of alumina to remove the t-butylcatechol inhibitor introduced with the reactants. The resulting product mixture was distilled in a wiped film evaporator at 3 mm Hg pressure at 90° C. to produce a light fraction containing unreacted vinylcyclohexene and dicyclopentadiene and the mono-adducts of 4-vinylcyclohexene and cyclopentadiene. A 150 g sample of this distillate was vacuum distilled using a 10-tray Oldershaw column to give four fractions. The fourth fraction, 65 g, was shown by gas chromatographic analysis to consist of 0.15% dicyclopentadiene, 88.3% endo-5-(3-cyclohexen-1-yl)-2-norbornene, 6.1% exo-5-(3-cyclohexen-1-yl)-2-norbornene and two additional components present in the amount of 1.9% and 2.4% which are believed to be isomeric adducts of the formula

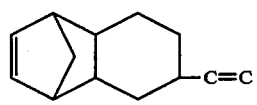

several additional components totalling about 0.4%, 0.4% tricyclopentadiene and about 0.4% unidentified components. Analysis of the fraction by nuclear magnetic resonance indicated about 87 mole percent of the endo adduct, about 9 mole percent of the exo adduct and about 5% of the isomeric adducts.

EXAMPLE 2

Preparation of Monoadduct Polyphenol

To a reactor equipped with a stirrer, condensor and additional funnel were added 188.2 g (2.0 mole) of phenol and 1.0 g of $BF_3$ $Et_2O$. The mixture was heated to 70° C. and 13.67 g of 5-(3-cyclohexen-1-yl)bicyclo[2.2.1]hept-2-ene was added over a 20-minute period. The temperature was raised to 150° C. over a 1 ½-hour period and was held for about 2 ½ hours. Unreacted phenol was distilled off. The recovered polyphenol had a terminal hydroxyl group concentration of 0.495 equivalent/100 g and a melting point of 70°–80° C.

EXAMPLE 3

Preparation and Curing of Epoxy Resin A

A mixture of 200 g of a polyphenolic addition product of phenol and 5-(3-cyclohexen-1-yl)bicyclo[2.2.1-]hept-2-ene prepared by a process as described in Example 1, 200 g of epichlorohydrin and 4.4 g of ethyltriphenylphosphonium bromide was placed in a 2 L round-bottomed flask equipped with a mechanical stirrer and condensor. The mixture was heated with stirring to 100 and was maintained at 100°–110° C. for 4 hours. The reaction mixture was then cooled to 80°–90° C. 150 ml of toluene and 88 g of 50% NaOH solution were added dropwise with distillation of $H_2O$. The toluene and excess epichlorohydrin were removed under reduced pressure to provide 235.8 g of a liquid resin (WPE 292). The product epoxy resin can be represented structurally as

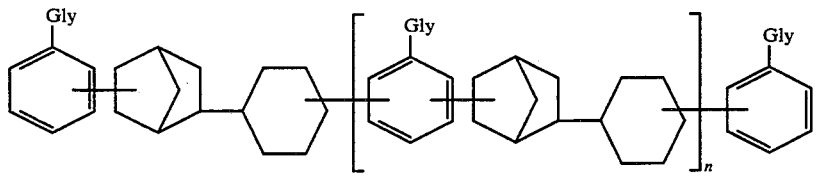

Heating 61.86 g of the product with 13.14 g 4,4'-diaminodiphenyl sulfone curing agent at 180° C. for 2 hours, 200° C. for 2 hours and 220° C. for 2 hours gave a cured material having the physical properties shown in Table 1.

EXAMPLE 4

Preparation of Diadduct Polyphenol

To a reactor equipped with a stirrer, condensor and addition funnel were added 376 g (4.0 mole) of phenol and 2.0 g of $BF_3$ $Et_2O$. The reaction mixture was heated to 70° C., and 48 g (0.2 mole) of diadduct was added over a 20-minute period. The temperature was raised to 150° C. over a 1 ½-hour period and held for about 2 ½ hours. Unreacted phenol was distilled. The recovered product had a melting range of 85°–95° C.

EXAMPLE 5

Preparation and Cure of Epoxy Resin B

The procedure described in Example 3 was repeated starting with 220 g of a polyphenol prepared by a process as described in Example 4 (hydroxyl content 0.44 eq/100 g), 4.4 g ETPPB and 220 g ECH in 150 ml of toluene. 248 g of epoxy resin B was isolated as a solid product having a melting point of 65°–70° C. and WPE OF 342.

Heating 59.26 g of the product with 10.74 g of 4,4'-diaminodiphenyl sulfone at 180° C. for 2 hours, 200° C. for 2 hours and 220° C. for 2 hours gave a cured material having the physical properties shown in Table 1. The product epoxy resin can be represented structurally as

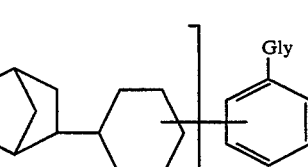

EXAMPLE 6

Preparation of Dicyclopentadiene Polyphenol (Comparison)

To a reactor equipped with a stirrer, condensor and addition funnel were added 188.2 g (2.0 mole) of phenol and 1.0 g of $BF_3$-$Et_2O$. The reaction mixture was heated to 70° C., and 13.2 g (0.1 mole) of dicyclopentadiene was added over a 20-minute period and held for 2 ½ hours. Unreacted phenol was distilled. The recovered product had a melting range of 115°–120° C. and a phenolic hydroxyl content of 0.62 eq/100 g.

EXAMPLE 7

Preparation and Cure of Epoxy Resin C (Comparison)

The procedure described in Example 3 was repeated starting with 25 g of a polyphenol prepared by a process as described in Example 6 (0.62 eq. OH/100 g), 41.3 g ECH and 0.7 g ETPPB. 25 g of epoxy resin C (WPE 260) was isolated.

Curing 9.92 g of the material with 2.37 g of diaminodiphenyl sulfone according to the cure schedule described in Example 3 gave a cured resin having the physical properties shown in Table 1.

TABLE 1

| Comparison of Physical Properties of Resins A, B and C | | | |
|---|---|---|---|
| | A | B | C |
| Tg (°C.) | | | |
| DSC | 180 | 198 | 196 |
| DMA | 190 | 210 | 210 |
| Flex Properties (RT/Dry) | | | |
| Strength (ksi) | 18.3 | 18.0 | 20.5 |
| Modulus (ksi) | 478 | 442 | 442 |
| Elongation (%) | 4.3 | 4.5 | 5.7 |
| Flex Properties (Hot/Wet) | | | |
| Strength (ksi) | 12.4 | 12.9 | 12.0 |
| Modulus (ksi) | 408 | 371 | 382 |
| Elongation (%) | 3.3 | 3.8 | 3.4 |
| Modulus Retention (%) | 85 | 84 | 86 |
| Fracture Toughness (Kq) | 463 | 486 | — |
| Moisture Gain (%) | | | |
| 200 hr. | 1.43 | 1.35 | 1.87 |
| 14 days | 1.48 | 1.37 | 1.98 |
| Dielectric Constant | 3.31 | 3.31 | — |
| Viscosity at 100° C. (cps) | 170–180 | 1500 | 170–180 |

We claim:
1. A composition comprising
(a) an epoxy resin of the formula

in which Gly is a glycidyl ether group, Ar is a $C_{6-20}$ aromatic moiety, L is a divalent cyclohexanenorbornane linking moiety, L' is a divalent cycloaliphatic linking moiety, and each of m and n is a number with the range of 0 to about 10; and
(b) a curing agent for the epoxy resin.
2. The composition of claim 1 in which the curing agent comprises diaminodiphenyl sulfone.
3. The composition of claim 1 in which the curing agent comprises methylene dianiline.
4. The solid product of subjecting the composition of claim 1 to a temperature of at least about 150° C. for at least about 0.25 hour.

* * * * *